United States Patent [19]

Ptchelintsev

[11] Patent Number: 5,728,733
[45] Date of Patent: Mar. 17, 1998

[54] N-ACYL-ETHYLENE TRIACETIC COMPOSITION FOR TREATING ABNORMAL KERATINIZATION

[75] Inventor: Dmitri Ptchelintsev, Mahwah, N.J.

[73] Assignee: Avon Products, Inc., Suffern, N.Y.

[21] Appl. No.: 762,716

[22] Filed: Dec. 10, 1996

Related U.S. Application Data

[62] Division of Ser. No. 549,419, Oct. 27, 1995, Pat. No. 5,621,008.
[51] Int. Cl.$^6$ .................. A01N 37/02; A61K 31/225
[52] U.S. Cl. .................. 514/547; 514/529; 514/530; 514/531; 514/546
[58] Field of Search ................... 514/547, 529, 514/530, 531, 546

[56] References Cited

U.S. PATENT DOCUMENTS

| | | |
|---|---|---|
| 3,879,537 | 4/1975 | Van Scott et al. . |
| 4,105,783 | 8/1978 | Yu et al. . |
| 4,363,815 | 12/1982 | Yu et al. . |
| 4,386,104 | 5/1983 | Nazzaro-Porro . |
| 4,885,282 | 12/1989 | Thornfeldt . |
| 4,973,473 | 11/1990 | Schneider et al. . |
| 5,084,270 | 1/1992 | Ciaudelli . |
| 5,177,243 | 1/1993 | Parker . |
| 5,191,081 | 3/1993 | Parker . |
| 5,191,106 | 3/1993 | Parker . |
| 5,250,728 | 10/1993 | Parker et al. . |
| 5,258,391 | 11/1993 | Van Scott et al. . |
| 5,284,972 | 2/1994 | Parker et al. . |
| 5,385,938 | 1/1995 | Yu et al. . |
| 5,385,943 | 1/1995 | Nazzaro-Porro . |
| 5,407,958 | 4/1995 | Heath et al. . |

*Primary Examiner*—Rebecca Cook
*Attorney, Agent, or Firm*—Hopgood, Calimafde, Kalil & Judlowe, LLP

[57] ABSTRACT

Disclosed is the novel use of N-acyl-N,N',N'-ethylenediaminetriacetic acids and N-acyl-N,N',N'-(ethylenedioxy) diethylenedinitrilotriacetic acids as active ingredients in preventative as well as therapeutic topical compositions to promote exfoliation and alleviate symptoms of skin conditions caused by abnormal keratinization.

8 Claims, No Drawings

N-ACYL-ETHYLENE TRIACETIC COMPOSITION FOR TREATING ABNORMAL KERATINIZATION

RELATED CASES

This is a divisional of application Ser. No. 549,419, filed Oct. 27, 1995, now U.S. Pat. No. 5,621,008.

FIELD OF INVENTION

The present invention relates to novel use of N-acyl-N,N',N'-ethylenediaminetriacetic acids and N-acyl-N,N',N'-(ethylenedixoy) diethylenedinitrilotriacetic acids, and their physiologically acceptable salts and derivatives, as ingredients in topical compositions for prevention and treatment of skin disorders associated with abnormal keratinization.

BACKGROUND OF THE RELATED ART

Abnormal keratinization is associated with the stratum corneum layer of the epidermis. The stratum corneum layer is composed of clear, dead squamous epithelial cells called corneocytes. Abnormal keratinization often appears as areas of scale-like buildup on the external skin surface and is the result of accumulated cell debris and dried keratohyalin from the cytoplasm of the dead, desquamated corneocyte cells.

The term "keratosis" is a microscopic term for describing the various ideological forms which contribute to abnormal skin keratinization such as "hyperkeratosis" which is hyperplasia of the stratum corneum seen with magnification. Whatever the ideology, the buildup of keratin is often undesirable, and a need exists in the art for an improved method of decreasing cohesion of corneocytes and promoting exfoliation of the cornified layers from the stratum corneum.

Topical compositions for treating skin disorders associated with disturbed keratinization are known. For example, U.S. Pat. Nos. 3,879,537, 4,105,783, 4,363,815, 5,258,391 and 5,385,938 describe the use of alpha-hydroxy acids and alpha-keto acids for treatment of a plethora of skin ailments including keratinization problems.

U.S. Pat. Nos. 4,386,104 and 5,385,943 describe the use of alpha, omega-n-alkane dicarboxylic acids with 7 to 13 carbon atoms and their physiologically acceptable forms to treat acne and keratoses such as presbyderma. U.S. Pat. No. 4,885,282 claims the use of mono- and di-carboxylic acids containing 4 to 18 carbons, their mercapto derivatives as well as salts and esters for treatment of ichthyosis with or without keratosis.

U.S. Pat. No. 4,973,473 teaches the use of a combination of carboxylic acid amides and a mucopolysaccharide as a moisturizer for treatment of dry skin. A topical composition, for treating dry skin, containing N-alkoxyalkylamides is described in U.S. Pat. No. 5,084,270; and U.S. Pat. No. 5,407,958 proposes the use of a composition containing an alpha-hydroxy acid neutralized with sodium hydroxymethyl-glycinate to treat dry, rough skin.

The known art does not describe use of N-acyl-N,N',N'-ethylenediaminetriacetic acids (hereinafter also "NEDAT") and N-acyl-N,N',N'-(ethylenedioxy) diethylenedinitrilotriacetic acids (hereinafter also "NEDENT") for prevention and treatment of abnormal skin keratinization, which the following description uniquely discloses.

OBJECTS OF THE INVENTION

The objects of the invention include the utilization of topical compositions containing as active ingredients, N-acyl-N,N',N'-ethylenediaminetriacetic acids (NEDAT acids), N-acyl-N,N',N'-(ethylenedioxy) diethylenedinitrilotriacetic acids (NEDENT acids), their physiologically acceptable salts, and derivatives of NEDAT and NEDENT acids, for prevention and treatment of skin conditions caused by abnormal keratinization.

Another object is to use NEDAT acids and/or NEDENT acids or their structural and chemical equivalents to decrease cohesion of corneocytes and promote exfoliation of the cornified layers of the stratum corneum.

Further objects include the use of NEDAT acids and/or NEDENT acids as active ingredients in topical compositions to alleviate skin conditions associated with abnormal keratinization such as hyperkeratinization, other thickenings of the skin associated with the stratum corneum layer such as corns and calluses, dry skin conditions such as xerosis, scaling associated with closed or open comedones, dandruff, ichthyosis, rough skin and fine wrinkling.

Other objects include the use of NEDAT acids and/or NEDENT acids as ingredients in topical compositions which also comprise other pharmaceutical and/or cosmetic active ingredients such as UV radiation absorbers or scatterers; other keratolytic agents and exfoliators; skin lightening agents; anti-aging compounds such as retinoic acid, retinol, isoretinoin, retinoid mimic, alpha-hydroxyacid or alpha-ketoacid; antifungal agents; antimicrobial agents; free radical scavengers such as tocopherol, tocopherol acetate, ascorbic acid, melatonin or butylated hydroxytoluene; anesthetic agents; self-tanning agents; constituents of skin lipids; and/or derivatives of ascorbic acid.

These and other objects will become more evident from the disclosure provided herein.

SUMMARY OF INVENTION

The invention provides a completely novel use for N-acyl-N,N',N'-ethylene-diaminetriacetic acids and N-acyl-N,N',N'-(ethylenedioxy) diethylenedinitrilotriacetic acids. During testing on human volunteers, it was surprisingly discovered that NEDAT and NEDENT acids, when applied topically, promote the exfoliation of the outermost layers of the stratum corneum.

For example, in exfoliation tests conducted, 0.2 wt % of NEDAT and NEDENT acids were more exfoliating and less irritating than other known exfoliators such as 0.5 wt % glycolic acid. Most acidic exfoliators are active at acidic pH's such as glycolic and lactic acids which are most active at pH's of about 3.8 to 4.2. When applied to sensitive skin, such acidic products have been known to produce sensory discomfort and mild skin reddening due to the necessary low pH.

In the present invention, the NEDAT and NEDENT acids are active exfoliators at neutral pH and can be formulated at pH's of about 7.0. Neutral pH is better tolerated by skin; and such neutral pH exfoliating compositions with NEDAT and NEDENT acids are mild and do not produce sensory discomfort, skin reddening or other indicia of sensitivity.

This description provides the exclusive disclosure that NEDAT and NEDENT acids, when topically applied, normalize stratum corneum desquamation and alleviate the symptoms of skin-conditions associated with disturbed keratinization. Accordingly, one aspect of the current invention is a composition containing as an active ingredient one or more of the N-acyl-N,N',N'-ethylenediaminetriacetic acids of general formula:

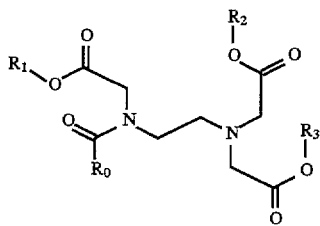

$R_o$ is an alkyl chain consisting of 2–18 carbons, substituted or unsubstituted, branched or non-branched, saturated or unsaturated, cyclic or alicyclic.

Preferred alkyl chains include ethyl, propyl, butyl, amyl, hexyl, heptyl, octyl, nonyl, decyl, undecyl, and dodecadecyl with dedecadecyl being the most preferred.

$R_1$, $R_2$ and $R_3$ are, together or separately, a hydrogen atom or an alkyl substituent consisting of 2–18 carbons. The sum of carbon atoms in $R_1$, $R_2$ and $R_3$ should not exceed 20.

In another embodiment, the invention is a composition containing as an active ingredient one or more of the N-acyl-N,N',N'-(ethylenedioxy) diethylenedinitrilotriacetic acids of the general formula:

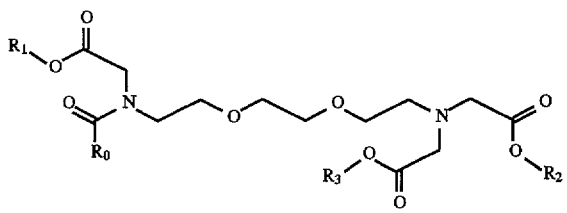

wherein, $R_o$ is an alkyl chain consisting of 2–18 carbons, substituted or unsubstituted, branched or non-branched, saturated or unsaturated, cyclic or alicyclic. Preferred alkyl chains include ethyl, propyl, butyl, amyl, hexyl, heptyl, octyl, nonyl, decyl, undecyl, and dodecadecyl with dodecadecyl being the most preferred.

$R_1$, $R_2$ and $R_3$ are, together or separately, a hydrogen atom or an alkyl substituent consisting of 2–18 carbons. The sum of carbon atoms in $R_1$, $R_2$ and $R_3$ should not exceed 24.

The NEDAT and NEDENT acids of this invention include free acids, their peroxides, amides, anhydrides, esters, organic or inorganic salts.

Therapeutic compositions of this invention may include one or more of the NEDAT and/or NEDENT acids from about 0.01 to 20.0 weight percent, preferably about 1.0 to 5.0 wt %, in an acceptable vehicle. The skin treatment composition of the invention may also include a therapeutically acceptable vehicle. The vehicle can be chosen from a variety of carriers normally used for topical administration and include, for example, surfactants, emulsifiers, stabilizers, emollients, thickeners, neutralizers, lubricants, and/or propellants; and can further comprise preservatives, skin penetration enhancers, humectants, chelating agents, colors and/or fragrances.

The composition may be in the form of solutions, water-in-oil or oil-in-water emulsions, suspensions, lotions, creams, sticks, ointments, liposomal complexes, polymer encapsulated powders, surface absorption complexes, aerosols, monomeric and polymeric gels, plasters, patches, films, tapes and other preparation known to those skilled in the art.

The amount of vehicle may vary from about 80.0 to about 99.99 wt %, preferably from about 95.0 to 99.0% by weight of total composition. To help with the dispersion of active NEDAT acids and/or NEDENT acids, the vehicle may contain emulsifiers. The emulsifying portion of the vehicle can be cationic, anionic, nonionic or amphoteric or a combination thereof. Nonionic emulsifiers are preferred. Exemplary nonionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates acyl isethionates.

Possible preservatives include parabens, sorbates, benzyl alcohol, diazolidinyl urea and isothiazolinones. Exemplary emollients suitable for the composition include silicon oils, mineral oil, cocoa butter, fatty acid esters, beeswax and lanolin. Examples of suitable thickening agents include xantham gum, xantham gum-brine tolerant, hydroxypropyl cellulose, hydroxyethyl cellulose, carbopol and gum acacia. An exemplary thickening agent is Sepigel 305 from Seppic Co., France. The composition may also include humectants, for example, glycerin, propylene glycol, polyethylene glycols and urea.

Cosmetic and pharmaceutical agents can be used in combination with NEDAT and NEDENT acids and those that can be incorporated into the composition include keratolytic agents such as, by way of example, salicylic acid and benzoyl peroxide; skin lightening agents such as kojic acid, benzoquinone, PT-40, vitamin C or its derivatives; organic and inorganic sunscreens for instance, benzophenones, parsol 1789, parsol MCX, titanium dioxide, zinc oxide, and benzylidene camphor; retinoids such as retinol, retinoic acid, retinyl palmitate or synthetic retinoid mimics; hormones such as estriol, estradiol, or hydrocortisone; alpha-hydroxyacids such as glycolic and lactic acids; vitamins (e.g. vitamin K, vitamin E, vitamin E acetate); antifungals (e.g. clotrimazole, ketoconazole, miconazole, naftifine, tolnaftate); tanning agents (e.g. dihydroxy-acetone); corticosteroids; antibiotics (e.g. erythromycin: tetracycline, cephalosperins); topical analgesics (e.g. lidocane); ceramides; and essential fatty acids.

The pH of the composition may be in the range between about 3 and about 8, more preferred between about 3.8 and 7.5 and most preferred between about 6.5 and 7.5. It was found that dissolution of NEDAT acid in hydrophilic vehicles such as hydroalcoholic solutions, occurs most rapidly at a pH near neutral. The pH can be adjusted with a number of known neutralizers including solutions of ammonium, sodium or potassium hydroxides, triethanolamine, sodium hydroxymethyl-glycinate, amphoteric amines such as amino acids (e.g. lysine), peptides, and salts of strong bases and weak acids (e.g. sodium bicarbonate, sodium biphosphate).

DETAILED DESCRIPTION OF THE INVENTION

EXAMPLE 1

Synthesis of NEDAT and NEDENT Acids

The N-acyl-N,N',N'-ethylenediaminetriacetic acids and N-acyl-N,N',N'-(ethylenedixoy) diethylenedinitrilotriacetic acids used in the presently described topical compositions and method were synthesized following general organic chemistry principles and specific protocols available such as found in U.S. Pat. Nos. 5,177,243, 5,191,081, 5,191,106, 5,250,728 and 5,284,972.

EXAMPLE 2

Skin Exfoliation Patch Assay with Desquamation Test

The ability of N-acyl-N,N',N'-ethylenediaminetriacetic acid to decrease corneocytes' cohesion end promote shedding of cornified layers of stratum corneum was discovered during a one day exfoliation assay performed on twenty human panelists according to the procedures described below.

The test used was a single 24 hour period occlusive patching (Parke-Davis patch) on skin of the mid-back region of the panelists. Skin gradings were conducted immediately post and 24 hours after removal of the patch. The test focused primarily on the effect of N-acyl-N,N',N'-ethylenediaminetriacetic acid in a hydro-alcoholic vehicle on the stratum corneum, and specifically on exfoliation. The comparative controls were with a plain hydroalcoholic vehicle and with a hydroalcoholic solution of glycolic acid, a known exfoliation enhancer.

A desquamation sampling was taken following the visual grading at 24 hours after removal of the patch. The test sites were first blotted with an acetone solution and allowed to dry prior to taking the desquamation sample. A rectangular facial cleansing wipe saturated with acetone was used. The desquamation wipe was placed on the test site and gently rubbed with thumb using even, equalized pressure. It was then removed and placed on a desquamation card. Corneocytes on the desquamation card were quantified using a Quantitative Exfoliation Score ("QES").

QES is a single number depicting overall exfoliation in terms of the cumulative total number of persons exhibiting exfoliation, the degree (area) of exfoliation, and the type of exfoliation (thin vs. thick—thick exfoliation is given a higher score). Any site exhibiting a "0" (no exfoliation) and which has been preceded by definite exfoliation was viewed as a site which had "shed" its scaliness. In this case, the preceding exfoliation score was "carried over" (accumulated) until the end of the test.

Specifically, the monosodium salt of N-lauroyl-N,N',N'-ethylenediaminetriacetic acid was dissolved in a 75:25 mixture of ethyl alchol and water in an amount sufficient to achieve w/w concentration of N-lauroyl-N,N',N'-ethylenediaminetriacetic acid sodium salt of 0.2 wt %. The pH of the solution was originally acidic and the dissolution of NEDAT acid monosodium salt was slow. The rate of dissolution was increased by adjusting the pH to 7.0 with dilute ammonium hydroxide solution and complete dissolution of NEDAT acid was observed.

The exfoliating potential of 0.2 wt % solution of NEDAT acid sodium salt was then compared to the exfoliating activity of control (1)—the vehicle (75:25=EtOH:$H_2O$, pH=7.0); and control (2)—an exfoliating solution of glycolic acid prepared at its optimum pH of 3.8. Each of the three solutions was applied to the skin of 20 human panelists and exfoliating activity was evaluated as described above. The results are summarized in Table 1.

TABLE 1

The following tabulates the desquamation score of N-lauroyl-N,N',N'-ethylenediaminetriacetic acid sodium salt solution vs. that for controls, glycolic acid and plain vehicle.

| TESTED SAMPLE | Desquam. SCORE | pH |
|---|---|---|
| 0.5 wt % Glycolic Acid (pH 3.8) | 3.56 | 0.62 |
| 0.2 wt % N-lauroyl-N,N', N'-ethylenediamine-triacetic acid sodium salt (pH 7.0) | 3.74 | 0.18 |
| EtOH:$H_2O$ (75:25) Vehicle (pH 7.0) | 3.56 | 0.09 |

The 0.2 wt % N-lauroyl-N,N',N'-ethylenediaminetriacetic acid sodium salt proved to be a superior exfoliator to both the vehicle or glycolic acid solution. Moreover, it was observed that the NEDAT acid sodium salt solution was producing more exfoliation than glycolic acid with less irritation. The tested panelists unanimously reported no discomfort with the NEDAT solution, but with the pH 3.8 glycolic acid solution, sensory discomfort and mild skin reddenings were noted, especially in panelists with sensitive skin.

EXAMPLE 3

Lotion NEDAT

This example illustrates a light lotion embodiment according to the present invention. It also demonstrates the feasibility of the combination of NEDAT acids with other active ingredients such as glycerin moisturizers. All %'s are expressed as (w/w) weight percents in Examples 3–5.

| | |
|---|---|
| N-acyl-N, N', N'-ethylenediaminetriacetic acid, sodium salt | 1.0% |
| Glycerine | 5.0% |
| Ammonium hydroxide | 2.5% |
| Thickener | 0.5% |
| Octylmethoxycinnamate | 2.0% |
| Polyoxyethylene (40 M) Stearate | 3.5% |
| Alcohol | 10.0% |
| Fragrance | 0.05% |
| Water | q.s.* |

*q.s. is balance 100 wt % with water.

EXAMPLE 4

Cream NEDAT

This example illustrates a cream embodiment using NEDAT as the active ingredient according to the invention.

| | |
|---|---|
| N-acyl-N,N',N'-ethylenediaminetriacetic acid | 2.5% |
| Mineral oil | 2.0% |
| Shea butter | 0.5% |
| Cyclomethicone pentamer | 10.0% |
| Cyclomethicone/Dimethicone copolyol | 11.5% |
| Propylene glycol | 2.5% |
| Sodium chloride | 1.0% |
| Sepigel | 0.5% |
| Neutralizing agent | to pH = 7 |
| Germall | 0.15% |
| Fragrance | 0.15% |
| Water | q.s. |

EXAMPLE 5

Alcoholic Lotion NEDAT

This example illustrates an alcoholic lotion embodiment according to the preset invention, and also a combination with other actives such as salicylic acid and bisabolol.

| | |
|---|---|
| N-acyl-N,N',N'-ethylenediaminetriacetic acid, monosodium salt | 1.5% |
| Ethanol | 56.0% |
| Butylated Hydroxytoluene | 0.01% |
| Propylene Glycol | 3.0% |
| Isopropyl myristate | 1.0% |
| Glycerine | 3.0% |
| Salicylic acid | 1.5% |
| Bisabolol | 1.0% |

-continued

| | |
|---|---|
| Ammonium Hydroxide | to pH = 7 |
| Uvinul D-50 | 0.02% |
| EDTA | 0.02% |
| Fragrance | 0.20% |
| Color | 0.05% |
| Water | q.s. |

Various modifications and alterations to the present invention may be appreciated based on a review of this disclosure. These changes and additions are intended to be within the scope and spirit of this invention as defined by the following claims.

What is claimed is:

1. A topical formulation for prevention and treatment of skin disorders associated with abnormal keratinization comprising N-acyl-N,N',N'-(ethylenedioxy) diethylenedinitrilotriacetic acid or a physiologically acceptable salt thereof.

2. The topical formulation of claim 1, wherein said N-acyl-N,N',N'-N-acyl-N,N',N'-ethylenedioxy diethylenedinitrilotriacetic acid has the following structure:

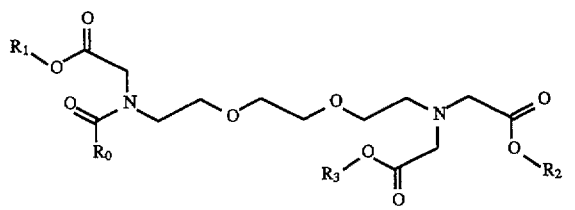

wherein, $R_o$ is an alkyl chain consisting of 2–18 carbons, substituted or unsubstituted, branched or non-branched, saturated or unsaturated, cyclic or alicyclic; and $R_1$, $R_2$ and $R_3$ are, together or separately, a proton or an alkyl substituent consisting of 2–18 carbons in which the sum of carbon atoms in $R_1$, $R_2$ and $R_3$ does not exceed 24.

3. The topical formulation of claim 2, in which said acid has an $R_o$ which is an alkyl chain selected from the group consisting of ethyl, propyl, butyl, amyl, hexyl, heptyl, octyl, nonyl, decyl, undecyl and dodecadecyl.

4. A method for treating skin conditions caused by abnormal keratinization comprising the steps of:

(a) applying to skin having areas of abnormal keratinization, a topical formulation comprising a suitable topical vehicle and an N-acyl-N,N',N'-(ethylenedioxy) diethylenedinitrilotriacetic acid or a physiologically acceptable salt thereof; and (b) allowing said topical formulation to decrease cohesion of corneocytes and promote exfoliation of cornified layers of the stratum corneum layer of said skin having areas of abnormal keratinization.

5. The method of claim 4, wherein said N-acyl-N,N',N'-N-acyl-N,N',N'-ethylenedioxy diethylenedinitrilotriacetic acid has the following structure:

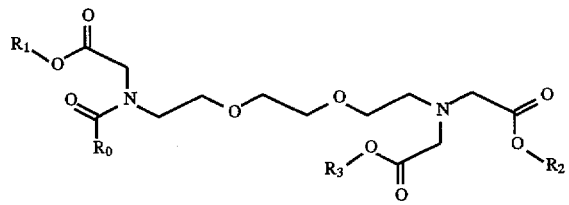

wherein, $R_o$ is an alkyl chain consisting of 2–18 carbons, substituted or unsubstituted, branched or non-branched, saturated or unsaturated, cyclic or alicyclic; and $R_1$, $R_2$ and $R_3$ are, together or separately, a proton or an alkyl substituent consisting of 2–18 carbons in which the sum of carbon atoms in $R_1$, $R_2$ and $R_3$ does not exceed 24.

6. The method of claim 5, in which said acid has an $R_o$ which is an alkyl chain selected from the group consisting of ethyl, propyl, butyl, amyl, hexyl, heptyl, octyl nonyl, decyl, undecyl and dodecadecyl.

7. The method of claim 4, wherein said topical formulation comprising a suitable topical vehicle, comprises an N-acyl-N,N',N'-(ethylenedioxy) diethylenedinitrilotriacetic acid or a physiologically acceptable salt thereof; and another compound selected from the group consisting of a keratolytic agent; a skin lightening agent; a sunscreen; an anti-aging compound; an antifungal agent; an antibiotic; a free radical scavenger; a tanning agent; a topical analgesic; a constituent of skin lipids; a hormone; a vitamin; a corticosteroid; a ceramide; and an essential fatty acid.

8. The method of claim 7, wherein said keratolytic agent is selected from the group consisting of salicylic acid and benzoyl peroxide;

said skin lightening agent is selected from the group consisting of kojic acid, benzoquinone and PT-40;

said sunscreen is selected from the group consisting of benzophenone, parsol 1789, parsol MCX, titanium dioxide, zinc oxide and benzylidene camphor;

said anti-aging compound is selected from the group consisting of retinoic acid, retinol, isoretinoin, retinyl palmitate, a synthetic retinoid mimic, alpha-hydroxyacid and alpha-ketoacid;

said anti-fungal agent is selected from the group consisting of clotrimazole, ketoconazole, miconazole, naftifine and tolnaftate;

said antibiotic is selected from the group consisting of erythromycin, tetracycline and cephalosporin;

said free radical scavenger is selected from the group consisting of tocopherol, tocopherol acetate, ascorbic acid, melatonin and butylated hydroxytoluene;

said tanning agent is dihydroxyacetone;

said topical analgesic is lidocaine;

said hormone is selected from the group consisting of estriol, estradiol and hydrocortisone; and said vitamin is selected from the group consisting of vitamin K and vitamin E.

* * * * *